Figure 1:
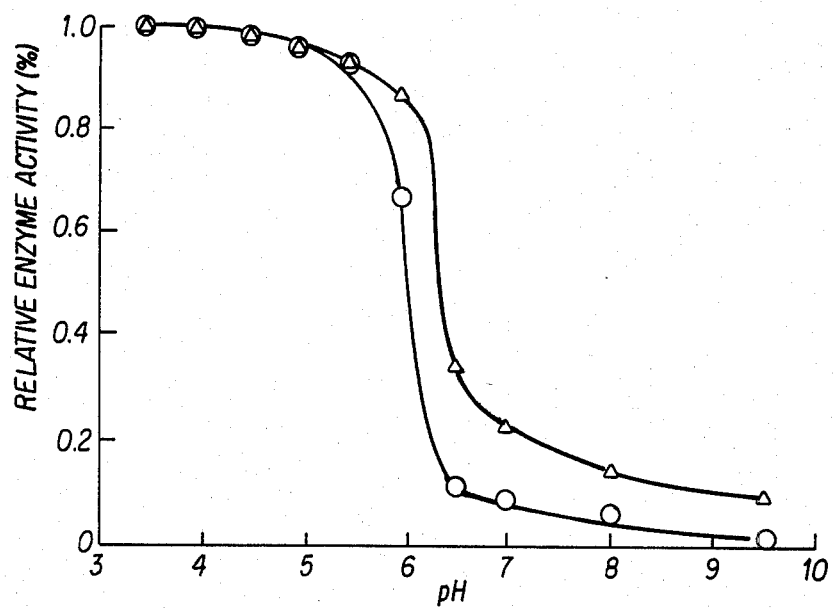

United States Patent [19]

Imanaka et al.

[11] Patent Number: 4,517,299
[45] Date of Patent: May 14, 1985

[54] ACETYLESTERASES

[75] Inventors: Hiroshi Imanaka, Osaka; Toshio Miyoshi, Fuji; Toshio Konomi, Tsushima; Yoshiaki Kubochi; Seiziro Hattori, both of Aichi; Takeshi Kawakita, Tsu, all of Japan

[73] Assignee: Fujisawa Pharmaceutical Co., Ltd., Osaka, Japan

[21] Appl. No.: 500,883

[22] Filed: Jun. 3, 1983

Related U.S. Application Data

[62] Division of Ser. No. 283,962, Jul. 16, 1981, Pat. No. 4,414,328.

[30] Foreign Application Priority Data

Jul. 21, 1980 [GB] United Kingdom ................. 8023834

[51] Int. Cl.³ .............................................. C12N 9/18
[52] U.S. Cl. ..................................................... 435/197
[58] Field of Search ................................. 435/47, 197

[56] References Cited

U.S. PATENT DOCUMENTS 3,749,641 7/1973 Takahashi et al. ................... 435/47
3,976,546 8/1976 Smith et al. ........................... 435/47

Primary Examiner—Alvin E. Tanenholtz
Attorney, Agent, or Firm—Oblon, Fisher, Spivak McClelland & Maier

[57] ABSTRACT

New acetylesterases are prepared from *Aureobasidium pullulans* IFO 4466 which are capable of hydrolyzing cephalosporin C to deacetylcephalosporin C.

1 Claim, 5 Drawing Figures

ACETYLESTERASES

This is a division of application Ser. No. 283,962, filed July 16, 1981, now U.S. Pat. No. 4,414,328.

This invention relates to a new process for the preparation of deacetylcephalosporin C by an enzymatic deacylation of cephalosporin C. More particularly, it relates to a new process for the preparation of deacetylcephalosporin C or its salt by contact of cephalosporin C or its salt with new esterase of a strain belonging to the genus Aureobasidium.

A process of this invention is expressed by the following reaction scheme:

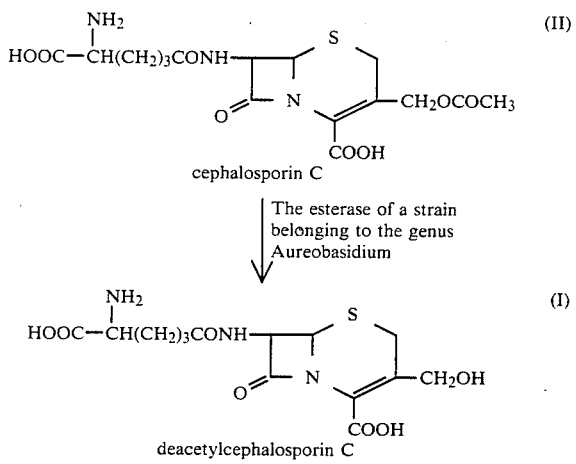

The object compound (I) of the present process, i.e. deacetylcephalosporin C is known as a valuable and important intermediate for the syntheses of therapeutically useful cephalosporin compounds.

It is already known that deacetylcephalosporin C can be produced by deacetylation of cephalosporin C with esterases of various microorganisms, but those processes can not be said to be sufficient and useful for the industrial manufacture of the same.

This invention has been completed by extensive study of the inventors based on their new finding that the esterase produced by a strain belonging to the genus Aureobasidium has an activity to convert cephalosporin C by deacetylation into deacetylcephalosporin C in good yield, i.e. in a conversion rate of almost 100%.

According to this invention, deacetylcephalosporin C can be prepared by contact of cephalosporin C or its salt, in an aqueous medium, with the esterase of a strain belonging to the genus Aureobasidium until substantially all the cephalosporin C is deacetylated and isolation of deacetylcephalosporin C thus produced in solid form from the aqueous medium.

Preferred salts of cephalosporin C and deacetylcephalosporin C may be an alkali metal salt (e.g. sodium salt, potassium salt) or an alkaline earth metal salt (e.g. magnesium salt, etc.).

The strain belonging to the genus Aureobasidium to be used in the present invention may include all of the microorganisms belonging to the genus Aureobasidium which produce an esterase for hydrolyzing the ester linkage at 3rd position of cephalosporin C to produce deacetylcephalosporin C and is widely distributed in nature or kept in the culture collections. Accordingly, said strain can be isolated from natural sources such as a soil sample or can also be selected from the collected cultures available in public facilities for culture collection.

As the representative example of said microorganism, there is exemplified Aureobasidium pullulans IFO 4466, which is available from one of the culture collection, i.e. Institute for Fermentation, Osaka, Japan. This invention may also include, within its scope, the use of mutants produced from said microorganism by conventional mutation means such as X-rays, ultraviolet radiation, treatment with mutagenic agents (e.g. nitric acid, N-methyl-N'-nitro-N-nitrosoquanidine) and the like.

According to the process of this invention, it is to be noted that contact of cephalosporin C with the esterase of the microorganism can be conducted by various modes of the present process, which will be apparent from the following description.

As one mode of the present process, it is to be understood that contact of cephalosporin C with the esterase of the microorganism of this invention is conducted by the contact of cephalosporin C with the cultured broth which is obtained by conventional cultivation of the strain belonging to the genus Aureobasidium or the processed material thereof, in an aqueous medium.

Cultivation of the microorganism to be used in this invention can be generally conducted in a conventional manner, and it may be advantageously carried out under stirring with aeration. As a culture medium to be used, there may be used a nutrient one containing sources of assimilable carbon and nitrogen and inorganic salts. The preferred sources of carbon are, for example, glucose, sucrose, lactose, glycerol and starch. The preferred sources of nitrogen are organic nitrogen sources, for example, meat extract, peptone, gluten meal, corn meal, cotton-seed meal, soybean meal, corn steep liquor, yeast extracts, casaminic acid and amino acids, as well as inorganic nitrogen sources, for example, ammonium salts (e.g., ammonium nitrate, ammonium phosphate, etc.). If desired, mineral salts, for example, calcium carbonate, sodium or potassium phosphate, magnesium salts and copper salts, and various vitamines can be also used.

Suitable pH of the culture media, suitable cultivation temperature and suitable cultivation time vary with the kind of the microorganisms to be used. A desirable pH usually lies in a range of pH 5 to 8. The temperature is usually selected from about 20° C. to about 30° C., preferably about 25° C. The cultivation time is usually selected from 15 hours to 72 hours, preferably from 24 hours to 50 hours.

The cultured broth per se thus obtained and its processed material can be employed for the preparation of deacetyl cephalosporin C. The processed material of the cultured broth means any preparation, which is prepared from the said cultured broth in a conventional manner for elevating the enzyme activity and is capable of deacetylating cephalosporin C to deacetylcephalosporin C.

The estrase activity usually exits in mycelia. Therefore, the following preparations can be exemplified as a processed material of the cultured broth.

(1) Raw mycelia; separated from the cultured broth in conventional manners such as filtration and centrifugation
(2) dried mycelia; obtained by drying said raw mycelia in conventional manners such as lyophilization and vacuum drying (3) cell—free extract; obtained by destroying said raw or dried cells in conventional manners (e.g. autolysis of the mycelia using an organic solvent, grinding the mycelia with alumina, sea sand, etc. or treating the mycelia with super sonic waves)

(4) enzyme solutions; obtained by purification or partial purification of said cell-free extracts in conventional manners (e.g. column chromatography)

(5) immobilized mycelia or enzyme; prepared by immobilizing said mycelia or enzyme in conventional manners (e.g. a method using acrylamide, glass bead, ion exchange resin, etc.).

The reaction comprising contact of cephalosporin C with the enzyme can be conducted in an aqueous medium such as water or a buffer solution, that is, it can be usually conducted by dissolving or suspending the cultured broth or its processed material in an aqueous medium such as water or a buffer solution containing cephalosporin C.

Preferable pH of the reaction mixture, concentration of cephalosporin C, reaction time and reaction temperature may vary with properties of a cultured broth or its processed material to be used. Generally, the reaction is carried out at pH 3 to 7, preferably pH 3.5 to 5,at 20° to 40° C., preferably 25° to 37° C. for 2 to 50 hours.

In the reaction mixture, the concentration of cephalosporin C as a substrate may be preferably selected from a range of 0.1 to 100 mg/ml.

As an alternative way for contact of cephalosporin C with the esterase, there is provided another mode of the present process which may be more convenient in the industrial scale production. That is, cephalosporin C in a cultured broth of a cephalosporin C-producing microorganism per se, without isolating cephalosporin C from said broth, is directly brought into contact with mycelia in a cultured broth of the esterase-producing strain belonging to the genus Aureobasidium to produce deacetylcephalosporin C.

For this purpose, there may preferably be employed a mixed culture of a cephalosporin C-producing microorganism and the esterase-producing strain belonging to the genus Aureobasidium. The cephalosporin C-producing microorganixm includes *Cephalosporium acremonium,* which is known and available to the public (e.g. *Cephalosporium acremonium* ATCC 11550) and the like.

The mixed culture may preferably be conducted firstly by culturing a cephalosporin C-producing microorganism (e.g. Cephalosporium acremonium) in a medium, and then by inoculating, at an appropriate time, the esterase-producing strain belonging to the genus Aureobasidium into the said cultured broth of a cephalosporin C-producing microorganism and further continuing the cultivation till cephalosporin C thus accumulated in the broth is converted into deacetylcephalosporin C.

In other words, the mixed culture may preferably be started by inoculating the esterase-producing strain belonging to the genus Aureobasidium to a cultured broth of a cephalosporin C-producing microorganism at an appropriate time during the cultivation period of cephalosporin C-producing microorganism.

In the mixed culture step as explained above, it is to be noted that inoculation of the esterase-producing strain belonging to the genus Aureobasidium is preferably conducted by adding a culture broth of said strain to a cultured broth of a cephalosporin C-producing microorganism. It is further to be noted that an appropriate time for innoculating the esterase-producing strain may be set up in consideration of kinds of strains of both of the microorganisms and the cultivation conditions and actually according to pre-experiment for detecting a preferable conditions, and it can be said to be usually preferable time when mycelia of a cephalosporin C-producing microorganism grows and begins to increase in the medium and cephalosporin C per se begins to be produced and increased in the cultured broth. And, the time for inoculating the esterase-producing strain may be appropriately set up 2 to 6 days, preferably 3 to 5 days after the beginning of the cultivation of a cephalosporin C-producing microorganism.

The medium for the mixed culture contains substantially the same ingredients as those exemplified for the culture medium for the strain belonging to the genus Aureobasidium as mentioned above.

Suitable pH of the medium is usually adjusted within a range of 5–7 preferably 5–6. The temperature of the mixed culture is usually selected from about 20°–30° C., preferably about 25° C. The suitable cultivation time is usually at least more than two days.

The object compound thus produced in the reaction mixture or the mixed cultured broth may be isolated and purified in a conventional manner used in cephalosporin chemistry. As such a manner, there are exemplified methods of purification with appropriate solvents, concentration under reduced pressure, lyophilization, crystallization, recrystallization and treatment with anionic or cationic exchange resin or macroporous nonionic adsorption resin and the like.

As explained in details hereinabove, the inventors of this invention found out a new and effective process for the preparation of deacetylcephalosporin C which comprises contacting cephalosporin C or its salt with the esterase of a strain belonging to the genus Aureobasidium, particularly *Aureobasidium pullulans* IFO 4466. Following the above study, the inventors of this invention continued to make an extensive study for identifying the properites of the esterase of the genus Aureobasidium used in this invention and confirming the novelty of the same over esterase known in a pertinent prior art, so that they concluded that the esterase of the genus Aureobasidium is a new enzyme which is capable of hydrolyzing cephalosporin C to deacetylcephalosporin C.

In this respect, as a pertinent prior art, there can be cited U.S. Pat. No. 3,912,589 issued on Oct. 14, 1975, in which there is disclosed the esterase of the genus Rhodotorula which is capable of hydrolyzing cephalosporin C to deacetylcephalosporin C, and it is to be noted that the genus Rhodotorula is a close microorganism to the Aureobasidium of this invention in view that each of them is a kind of microorganisms belonging to "yeast".

The following is the detailed explanation properties of the exterase produced by a strain of the genus *Aureobasidium pullulans* IFO 4466, which is a representative strain belonging to the genus Aureobasidium, and the relevant matters.

PREPARATION OF THE ENZYME

The esterase was prepared by means of isolation and purification from a cultured broth of *Aureobasidium pullulans* IFO 4466, and the details of the preparation is referred to Example 3 as explained hereinafter.

As clearly seen from said Example 3, the esterase includes two components of enzymes, which are capable of hydrolyzing cephalosporin C to deacetylcephalosporin C, and is characterized by the property that the said esterases are capable of hydrolyzing an acetic ester, but are not capable of hydrolyzing an ester besides acetic ester, which will be apparent in the following. Accordingly, the esterase produced from *Aureobasidium pullulans* IFO 4466 should be named as so-called "acetylesterase", and so the inventors of this invention names two components of the esterases of this invention as Acetylesterase 4466-I and Acetylesterase 4466-II for convenience sake in the following explanation.

PROPERTIES OF THE ESTERASE

The Acetylesterase 4466-I and Acetylesterase 4466-II have the following enzymatic properties.
(1) Substrate Specificity (Acetylesterase 4466-I and 4466-II):
Hydrolyzable: Acetic ester
Not hydrolyzable: Ester besides acetic ester
The Substrate Specificity was determined by the following method.

The substrate (5 mg) as listed below was inserted into a test tube and dissolved in 0.05M acetate buffer solution (pH 4.5)(1 ml). To the solution was added the Enzyme solution A (i.e. Acetylesterase 4466-I) (0.1 ml) or B (i.e. Acetylesterase 4466-II)(0.1 ml) as prepared in the Example 3.

After the reaction mixture was incubated on a shaken at 25° C. for an hour, hydrolysis of the substrate was determined in the following manner.
(i) Analysis 1 (Thin layer chromatography)
Test solution (1 μl) and authentic sample were spotted on a silica gel plate, respectively. The plate was developed with 70% aqueous n-propanol and dried. Detection was carried out by ultraviolet absorption.
(ii) Analysis 2 (Gas chromatography)
Test solution was analyzed by gas chromatography in the following condition.
Column: SE. 30 lm
Carrier gas: $N_2$ (15 ml/minutes)
Column temperature: 80° C.
Injection temperature: 120° C.
Detector temperature: 80° C.
Detector: FID (Air 1.0 kg/cm$^2$G, $H_2$ 1.0 kg/cm$^2$G)
The results are shown in the following table.

| Substrate | Hydrolysis Acetylesterase 4466-I | Acetylesterase 4466-II | Analysis Method |
| --- | --- | --- | --- |
| Cephalosporin C | ++ | ++ | Analysis 1 |
| 7-Aminocephalosporanic acid | ++ | ++ | " |
| Cephapirin | ++ | ++ | " |
| Methyl acetate | + | + | Analysis II |
| Ethyl acetate | + | + | " |
| Methyl propionate | − | − | " |
| Methyl butyrate | − | − | " |
| Ethyl formate | − | − | " |

Note
++: Completely hydrolyzed
+: Partly hydrolyzed
−: Not hydrolyzed (2) Effect of pH
(A) Substrate: Cephalosporin C
  (a) Optimum pH: (Acetylesterase 4466-I and 4466-II) Below pH 4

As shown in Fiture 1 of accompanying drawings, optimum pHs of Acetylesterase 4466-I (o—o) and Acetylesterase 4466-II (Δ—Δ) are below pH 4.
Enzyme activities at various pH were measured by the following method.
(i) Buffer solution
pH 3.5–6.0: 0.05M acetate buffer solution
pH 5.0–8.0: 0.1M phosphate buffer solution
pH 7.0–9.5: 0.1M tris-hydrochloride buffer solution
(ii) Reaction
To the enzyme solution (0.5 ml), were added warm (30° C.) buffer solution (4 ml) at various pH as mentioned above and 5% cephalosporin C sodium dihydrate aqueous solution (0.5 ml). The reaction mixture was incubated on a shaker at 30° C. for an hour. Subsequently, produced deacetyl cephalosporin C and unreacted cephalosporin C were determined by high pressure liquid chromatography,
  (b) Stable pH range (Acetylesterase 4466-I and 4466-II): pH 4.0–6.0

Figure 2:
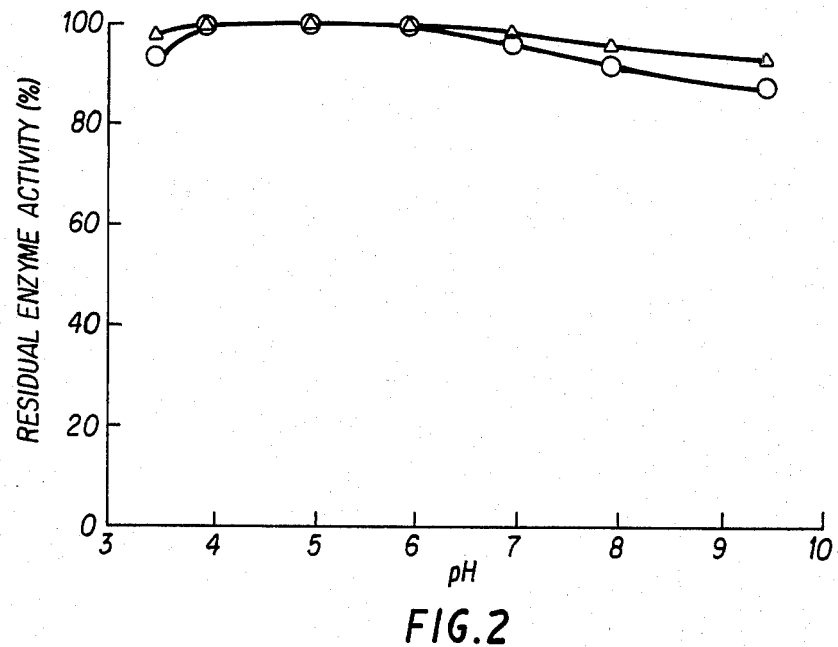

As shown in FIG. 2 of accompanying drawings, Acetylesterase 4466-I (o—o) and Acetylesterase 4466-II (Δ—Δ) are stable in a range of pH 4.0–6.0.
The stability test was carried out by the following method.
To the enzyme solution (1 ml), was added a buffer solution (9 ml) at various pH as mentioned above. The enzyme solution (10 ml) was heated at 60° C. for an hour. Subsequently, residual enzyme activity of the acetyl esterase was determined according to the Determination Method I as mentioned hereinafter.
  (B) Substrate: Ethyl acetate—Optimum pH (Acetylesterase 4466-I and 4466-II): Around pH 5.25

Figure 5:
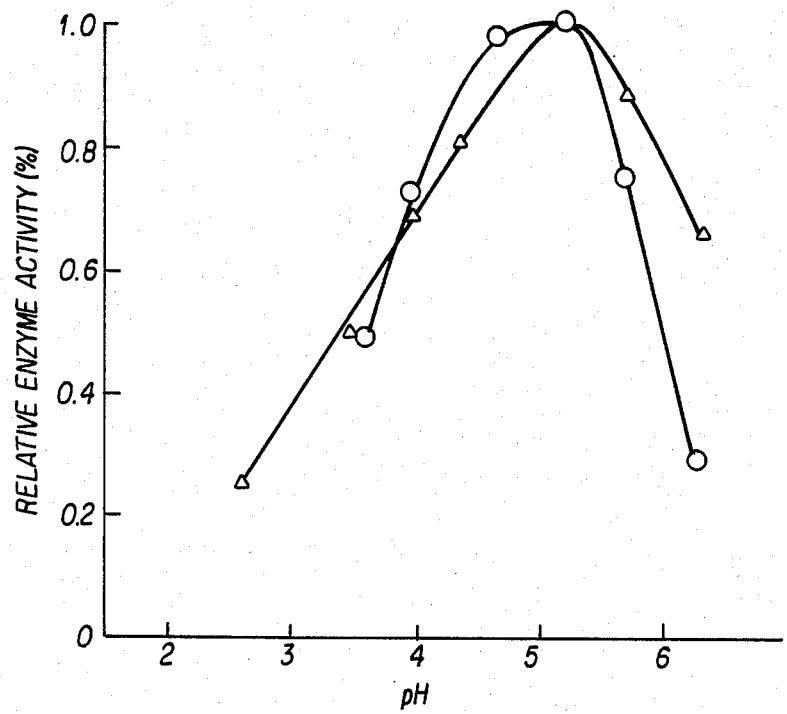

As shown in FIG. 5 of accompanying drawings, optimum pH of Acetylesterase 4466-I (o—o) and Acetylesterase 4466-II (Δ—Δ) are around pH 5.25 in case of using ethyl acetate as substrate.
Enzyme activity at various pH were measured by the following method.
To ethyl acetate (5 μl), were added warm (30° C.) buffer solution (1 ml) at various pH as mentioned above and the enzyme solution (300 μl). The reaction mixture was incubated on a shaker at 30° C. for an hour. Subsequently, produced ethanol and unreacted ethyl acetate were determined by gas chromatography.

Effect of Temperature
  (a) Optimum temperature (Acetylesterase 4466-I and 4466-II): Around 37° C.

Figure 3:
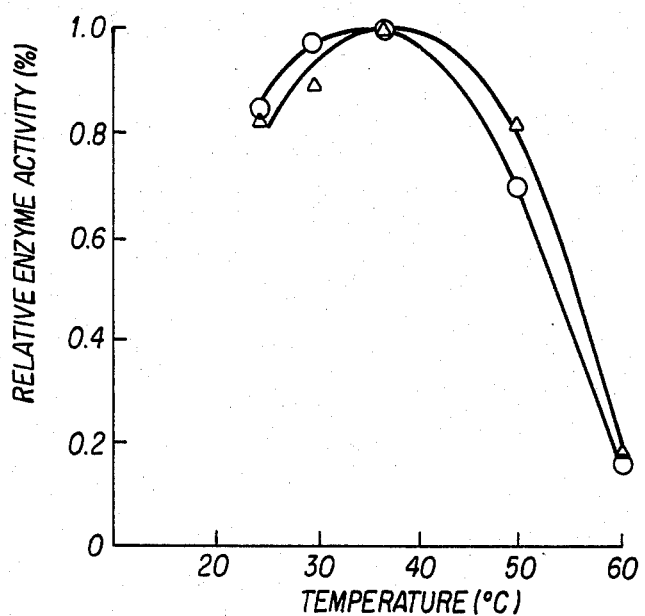

As shown in FIG. 3 of accompanying drawings, optimum temperature of Acetylesterase 4466-I (o—o) and Acetylesterase 4466-II (Δ—Δ) are around 37° C.
Enzyme activities at various temperature were measured by the following method.
To the enzyme solution (0.5 ml), were added 0.05M acetate buffer solution (pH 4.0)(4 ml), which was warmed at prescribed temperature, and 5% cephalosporin C sodium dihydrate aqueous solution (0.5 ml). The reaction mixture was incubated on a shaker at prescribed temperature for an hour. Subsequently, produced deacetyl cephalosporin C and unreacted cephalosporin C were determined by high pressure liquid chromatography,
  (b) Stable temperature range (Acetylesterate 4466-I and 4466-II): Below 60° C.

Figure 4:
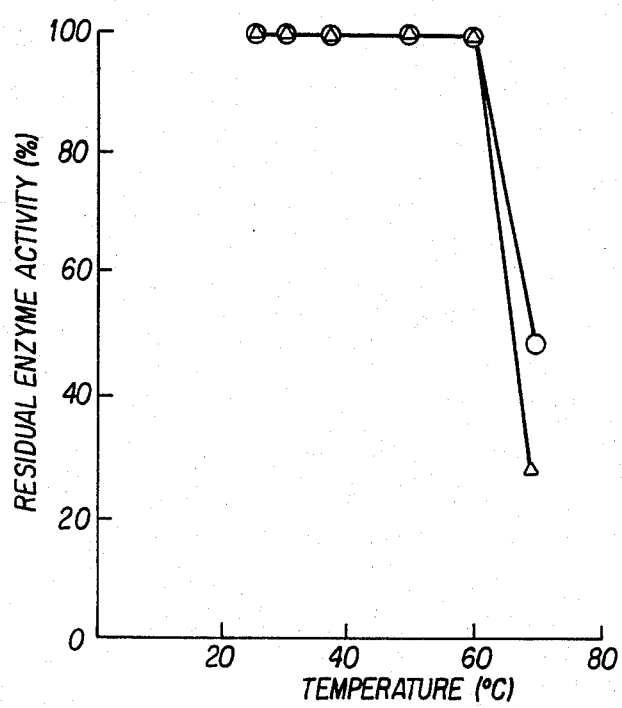

As shown in FIG. 4 of accompanying drawings, Acetylesterase 4466-I (o—o) and Acetylesterase 4466II (Δ—Δ) are stable below 60° C.

The stability test was carried out by the following method.

Enzyme solution (pH 4.0) was allowed to stand at prescribed temperature (25°–70° C.) for an hour. Subsequently, residual enzyme activities were determined according to Determination Method I as mentioned below.

(4) Determination of Km (In case that the substrate is cephalosporin C)

Acetylesterase 4466-I: Km=11.5 mM

Acetylesterase 4466II: Km=13.7 mM

Km values of Acetylesterase 4466-I and Acetylesterase 4466-II were determined in the following method.

To 0.05M acetate buffer solution (pH 4.0) containing cephalosporin C sodium dihydrate in a various concentration (0.2–5%)(4.5 ml), was added enzyme solution (0.5 ml).

The reaction mixture was incubated on a shaker at 30° C. for an hour. Subsequently, produced deacetyl cephalosporin C and unreacted cephalosporin C were determined by high pressure liquid chromatography. Km values of each esterase were calculated in a conventional manner.

(5) Effect of metal ion

Enzyme activities of Acetylesterase 4466-I and Acetylesterase 4466-II are not affected by metal ion such as $Cu^{2+}$, $Mn^{2+}$, $Mg^{2+}$, $Zn^{2+}$, $Ni^{2+}$, $Ca^{2+}$, $Ba^{2+}$, $Fe^{3+}$.

Effect of metal ion on the said acetylesterase was determined by the following method.

To the enzyme solution (0.5 ml), were added 0.05M acetate buffer solution (pH 4.0) containing one of metal ion as mentioned above ($5 \times 10^{-4}$ mol) and 5% cephalosporin C sodium dihydrate aqueous solution (0.5 ml). The reaction mixture was incubated on a shaker at 30° C. for an hour. Subsequently, produced deacetylcephalosporin C and unreacted cephalosporin C were determined by high pressure liquid chromatography.

As a control, there was used 0.05M acetate buffer solution (pH 4.0) containing no metal ion in the procedure as mentioned above.

Enzyme activity of esterases can be measured by the following method.

DETERMINATION METHOD I (a) Reaction

To the enzyme solution (0.5 ml), is added warm (30° C.) 0.05M acetate buffer solution (4 ml) and 0.05M acetate buffer solution (0.5 ml) containing cephalosporin C sodium dihydrate (50 mg/ml). The reaction mixture is incubated on a shaker at 30° C. for an hour. Subsequently, produced deacetyl cephalosporin C and unreacted cephalosporin C are determined by high pressure liquid chromatography in the following conditions, respectively.

Stationary phase: Polygosil 60-10 $C_{18}$ (trade mark, made by Sumitomo Chemical Co., Ltd.)

Mobile phase: A mixture of methanol, water and acetic acid (100:900:5)

Column height: 30 cm

Column temperature: Ambient temperature

Detector: Ultraviolet absorption at 250 nm

Flow rate: 1.0 ml/minutes

Enzyme activity (mg/hour.ml or mg) is expressed as deacetylcephalosporin C (mg) thus produced per an enzyme preparation (1 ml or 1 mg) in the above reaction condition.

(b) Calculation method of specific activity (i) Determination of protein content Protein content in an enzyme preparation can be determined according to Lawry method [cf. Journal of Biological Chemistry 193,265 (1951)] using bovine serum albumin as standard sample.

(ii) Calculation of specific activity

Specific activity can be calculated in the following equation.

$$\text{Specific activity} = \frac{\text{Enzyme activity (mg/hour} \cdot \text{ml or mg)}}{\text{Protein content (mg/ml or mg)}}$$

From the observation of the properties as explained hereinabove, it can be said that the acetylesterases of this invention have very unique properties, especially having a capacity of hydrolyzing cephalosporin C to deacetylcephalosporin C, very narrow substrate specificity (i.e. the said acetylesterases are capable of hydrolying only acetic ester, but are not capable of hydrolyzing the other ester) and unique optimum pH (i.e. said acetylesterases have considerable acidic pH) in comparison with known esterases.

Further, in comparison of the acetylesterase of this invention with a known esterase which is capable of hydrolyzing cephalosporin C to decetylcephalosporin C, i.e. the esterase produced by the genus Rodotorula, as the representative thereof, *Rodotorula glutinis* IFO 1125, it was observed that the acetylesterases of this invention (hereinafter referred to A.E.) are quite different from the esterase produced by the genus Rodotorula (hereinafter referred to R.E.), for example, in the following points. That is:

optimum pH of A.E. is below pH 4, while that of R.E. is around pH 5 to 6;

optimum temperature of A.E. is around 37° C., while that of R.E. is around 50° C; and stable pH range of A.E. is around pH 4.0 to 6.0, while that of R.E. is around pH 6.0

According to the extensive study and analysis of the results as mentioned above, the inventors of this invention concluded that Acetylesterase 4466-I and Acetylesterase 4466-II are new enzymes.

The following Examples are given for the purpose of illustrating the present invention.

EXAMPLE 1

An aqueous medium (pH 7.0) (100 ml) containing 1% of glucose, 0.3% of peptone and 0.3% of beef extract was poured into each of four 500 ml Erlenmeyer flasks and sterilized at 120° C. for 20 minutes. To each of the media was added a loopful of slant culture of *Aureobasidium pullulans* IFO 4466. The organism was grown on a shaker at 25° C. for 2 days.

Further, the same aqueous medium as mentioned above (20 liters) was poured into 30 liters jar-fermenter and sterilized at 120° C. for 20 minutes. To the medium was added whole volume of the cultured broth as obtained above.

The organism was grown at 25° C. for 2 days.

The cultured broth thus obtained was used in the following preparations of deacetylcephalosporin C.

(1) Preparation of deacetyl cephalosporin C using mycelia of *Aureobasidium pullulans*

The wet mycelia (10 g) which was obtained by centrifugation of the above cultured broth was added to an aqueous solution (300 ml) containing cephalosporin C sodium.dihydrate (25 mg/ml). The reaction mixture was stirred at pH 4.5 and 30° C. for 10 hours until cephalosporin C in the mixture disappeared. The resultant mixture was filtered. The filtrate was adjusted to pH 7.0 and concentrated under reduced pressure to give crystals, which was allowed to stand overnight at 5° C. To the crystals was added a small volume of 75% aqueous ethanol and the mixture was triturated.

The crystals were obtained by filtration and dried in vacuo to give crystalline deacetyl cephalosporin C (3.8 g).

IR spectrum of the crystals as obtained above was identical with that of the authentic deacetylcephalosporin C.

(2) Preparation of deacetylcephalosporin C using enzyme extracts from mycelia of *Aureobasidium pullulans*

To the wet mycelia (10 g) was added a small volume of chloroform. The mixture was allowed to stand at ambient temperature for 30 minutes. To the mixture was added distilled water (20 ml). After allowing to stand at ambient temperature for a day, the mixture was centrifuged to give enzyme extracts (20 ml). The enzyme extracts was added to an aqueous solution (300 ml) containing cephalosporin C sodium.dihydrate (25 mg/ml). The reaction mixture was stirred at pH 4.5 and 30° C. for 10 hours until cephalosporin C in the mixture disappeared. To the resultant mixture was added activated charcoal (3 g) and the mixture was filtered. The filtrate was adjusted to pH 7.0 and concentrated under reduced pressure to give crystals, to which was added a small volume of 75% aqueous ethanol and the mixture was triturated. The crystals were separated by filtration and dried in vacuo to give crystalline deacetylcephalosporin C (3.6 g).

IR spectrum of the crystals as obtained above was identical with that of the authentic deacetylcephalosporin C.

(3) Preparation of deacetylcephalosporin C using immobilized mycelia

The frozen and thawed mycelia (24 g) of *Aureobasidium pullulans* IFO 4466 was added to an aqueous solution (20 ml) containing acrylamide (7.5 g) and N,N'-methylenebisacrylamide (0.4 g).

To the mixture was added 5% aqueous N,N,N',N'-tetramethylethylenediamine (5 ml) and 1% aqueous ammonium persulfate (5 ml) at 4° C. in nitrogen atmosphere. The reaction mixture was polymerized in a glass tube at 4° C. for an hour. The polyacrylamide gel thus produced was pushed out and crushed with a crusher. The crushed gel was packed in a column (volume: 100 ml) and washed with 0.1M acetate buffer solution and cold water (1 liter). An aqueous solution (1 liter) containing cephalosporin C sodium.dihydrate (1.6 mg/ml) was passed through the column as prepared above in a rate of SV=0.5. After it was confirmed that no cephalosporin sodium.dihydrate existed in the passed solution, the passed solution was adjusted to pH 7.0, concentrated under reduced pressure and allowed to stand overnight at 5° C. To the residue was added 75% aqueous ethanol and mixed sufficiently to precipitate crystals, which were separated and dried in vacuo to give crystalline deacetylcephalosporin C (0.9 g).

IR spectrum of the crystals was identical with that of the authentic deacetylcephalosporin C.

EXAMPLE 2

An aqueous medium (pH 7.0)(100 ml) containing 3% of soybean meal, 2% of sucrose, 1% of glucose, 1% of corn steep liquor and 0.5% of calcium carbonate was poured into each of four 500 ml Erlenmeyer flasks and sterilized for 20 minutes at 120° C. On each of the media was inoculated a loopful of slant culture of *Cephalosporium acremonium* ATCC 11550. The organism was grown on a shaker at 30° C. for 5 days.

On the other hand, an aqueous medium (pH 7.0) (20 liters) containing 3% of peanut powder, 1% of soybean meal, 2% of corn steep liquor, 2% of methyl oleate, 0.5% of ammonium sulfate, 0.6% of DL-methionine, 2% of beet molasses, 2% of glucose and 0.8% of calcium carbonate was poured into 30 liters jar-fermenter and sterilized at 120° C. for 20 minutes. On the medium was inoculated whole volume of the cultured broth as obtained above. The organism was grown at 25° C. for 3 days.

Further, an aqueous medium (100 ml)(pH 7.0) containing 1% of glucose, 0.3% of peptone and 0.3% of beef extract was poured into each of four 500 ml Erlenmeyer flasks and sterilized at 120° C. for 20 minutes. On each of the media was inoculated a loopful of *Aureobasidium pullulans* IFO 4466. The organism was cultured at 25° C. for 2 days. The whole volume of this cultured broth was inoculated on the 3 days—cultured broth of *Cephalosporium acremonium* as obtained above and the mixed cultured broth was incubated at 25° C. for 2 days. Subsequently, the mixed cultured broth was analyzed by bioautography and bioassay using *Bacillus megaterium*. The result of the analysis showed the fact that all of the cephalosporin C in the cultured broth was converted to deacetylcephalosporin C and yield of deacetylcephalosporin C was 0.5 mg/ml.

EXAMPLE 3

The mycelia (350 ml) were collected by centrifuge from the cultured broth (10 liters) of *Aureobasidium pullulans* IFO 4466 which was prepared in substantially the same manner as described in Example 1. To the mycelia, was added one-fifth volume of chloroform.

The mixture was stirred for 30 minutes. Twice volumes of water were added to the mixture. The aqueous mixture was allowed to stand at 25° C. for 24 hours.

The mixture was filtered to give Enzyme extract I (1000 ml) and adjusted to pH 4.0 and then filtered to remove insoluble materials. The filtrate was subjected to a ultrafiltration using a membrane (Molecular weight: 0.1 million cut) to give a concentrate (80 ml), which was lyophilized to give a crude powder. The crude powder (4 g) was dissolved in 0.05M acetate buffer solution (pH 4.0)(20 ml) and passed through a column of CM-Sephadex C-25 (trade mark: made by Pharmacia AB, internal diameter of the column: 40 mm, height of the column: 675 mm) and the column was developed with the same acetate buffer solution as mentioned above (velocity: 64 ml/hour). The fraction (440 ml) containing the object compound was collected and passed through a column of DEAE-Sephadex A-25 (trade mark): made by Pharmacia AB, internal diameter of the column: 40 mm, height of the column: 785 mm). The column was washed with 0.05M acetate buffer solution (pH 4.0) (1000 ml) and developed with (0.05M–0.25M) acetate buffer solution (pH 4.0) in a linear gradient manner (velocity: 64 ml/hour) to give Fraction A (360 ml) and Fraction B (980 ml)

The Fraction A had 1.7-hold higher specific activity than the Fraction B. The Fraction A and Fraction B were concentrated by ultrafiltration and passed through a column of Sepharose 4B (trade mark; Pharmacia AB, internal diameter of the column: 29 mm, height of the column: 535 mm), respectively. Each column was developed with 0.05M acetate buffer solution (pH 4.0) to give Enzyme solution A (72 ml) from the Fraction A and Enzyme solution B (32 ml) from the Fraction B, respectively.

Each specific activity of the enzyme preparations as prepared above is given as a relative specific activity in the following table. In this respect, it is to be noted that said "relative specific activity" is indicated with a figure calculated on the criterion that the activity of the Enzyme Extract I shall be taken as a figure "1".

| Enzyme Preparation | Relative Specific Activity |
|---|---|
| Enzyme Extract I | 1 |
| Fraction A | 110 |
| Fraction B | 64 |
| Enzyme Solution A | 167 |
| Enzyme Solution B | 105 |

We claim:

1. An acetylesterase obtainable from *Aureobasidium pullulans* IFO 4466 selected from acetylesterase 4466-I having the properties of
    (a) Capability of hydrolyzing Cephalosporin C to deacetylcephalosporin C
    (b) Substrate Specificity
        Hydrolyzable: Acetic ester
        Not Hydrolyzable: Ester besides acetic ester
    (c) Optimum pH: Below pH 4
    (d) Stable pH range: pH 4.0–6.0
    (e) Optimum temperature: Around 37° C.
    (f) Stable temperature range: Below 60° C.
    (g) Km value: 11.5 mM and
    (h) Effect of metal ion: the enzyme activity is not affected by a metal ion selected from $Cu^{2+}$, $Mn^{2+}$, $Mg^{2+}$, $Zn^{2+}$, $Ni^{2+}$, $Ca^{2+}$, $Ba^{2+}$ and $Fe^{3+}$, provided that the substrate is cephalosporin C in the above (c)–(h), and Acetylesterase 4466-II having the properties of
    (a) Capability of hydrolyzing cephalosporin C to deacetylcephalosporin C
    (b) Substrate Specificity
        Hydrolyzable: Acetic ester
        Not Hydrolyzable: Ester besides acetic ester
    (c) Optimum pH: Below pH 4
    (d) Stable pH range: pH 4.0–6.0
    (e) Optimum temperature: Around 37° C.
    (f) Stable temperature range: Below 60° C.
    (g) Km value: 13.7 mM and
    (h) Effect of metal ion: The enzyme activity is not affected by a metal ion selected from $Cu^{2+}$, $Mn^{2+}$, $Mg^{2+}$, $Zn^{2+}$, $Ni^{2+}$, $Ca^{2+}$, $Ba^{2+}$ and $Fe^{3+}$, provided that the substrate is cephalosporin C in the above (c)–(h).

* * * * *